United States Patent [19]

Aude et al.

[11] 4,053,771
[45] Oct. 11, 1977

[54] METHOD AND DEVICE FOR ACTIVATION ANALYSIS

[75] Inventors: Georges Aude, Meylan; Jean Laverlochére, La Tronche, both of France

[73] Assignee: Commissariat a l'Energie Atomique, Paris, France

[21] Appl. No.: 636,631

[22] Filed: Dec. 1, 1975

[30] Foreign Application Priority Data

Dec. 6, 1974 France .............................. 74.40122

[51] Int. Cl.² .............................................. G01T 1/00
[52] U.S. Cl. .................................. 250/328; 250/303; 250/391
[58] Field of Search ................ 250/302, 328, 391, 303

[56] References Cited

U.S. PATENT DOCUMENTS

| | | | |
|---|---|---|---|
| 2,500,492 | 3/1950 | Henriques | 250/328 |
| 3,008,047 | 11/1961 | Early et al. | 250/302 |
| 3,188,469 | 6/1965 | Eukel | 250/302 |

*Primary Examiner*—Harold A. Dixon
*Attorney, Agent, or Firm*—McNenny, Pearne, Gordon, Gail, Dickinson & Schiller

[57] ABSTRACT

N samples are irradiated simultaneously for a period which is N times longer than the period of subsequent measurement of a sample, by means of a device constituted by a transfer circuit in which stations are provided successively for introduction, irradiation, separation, measurement and discharge of samples. A portion of the circuit serves to transfer a sample-holder for N samples, means for positioning the sample-holder and extracting samples therefrom being provided at the separating station.

10 Claims, 4 Drawing Figures

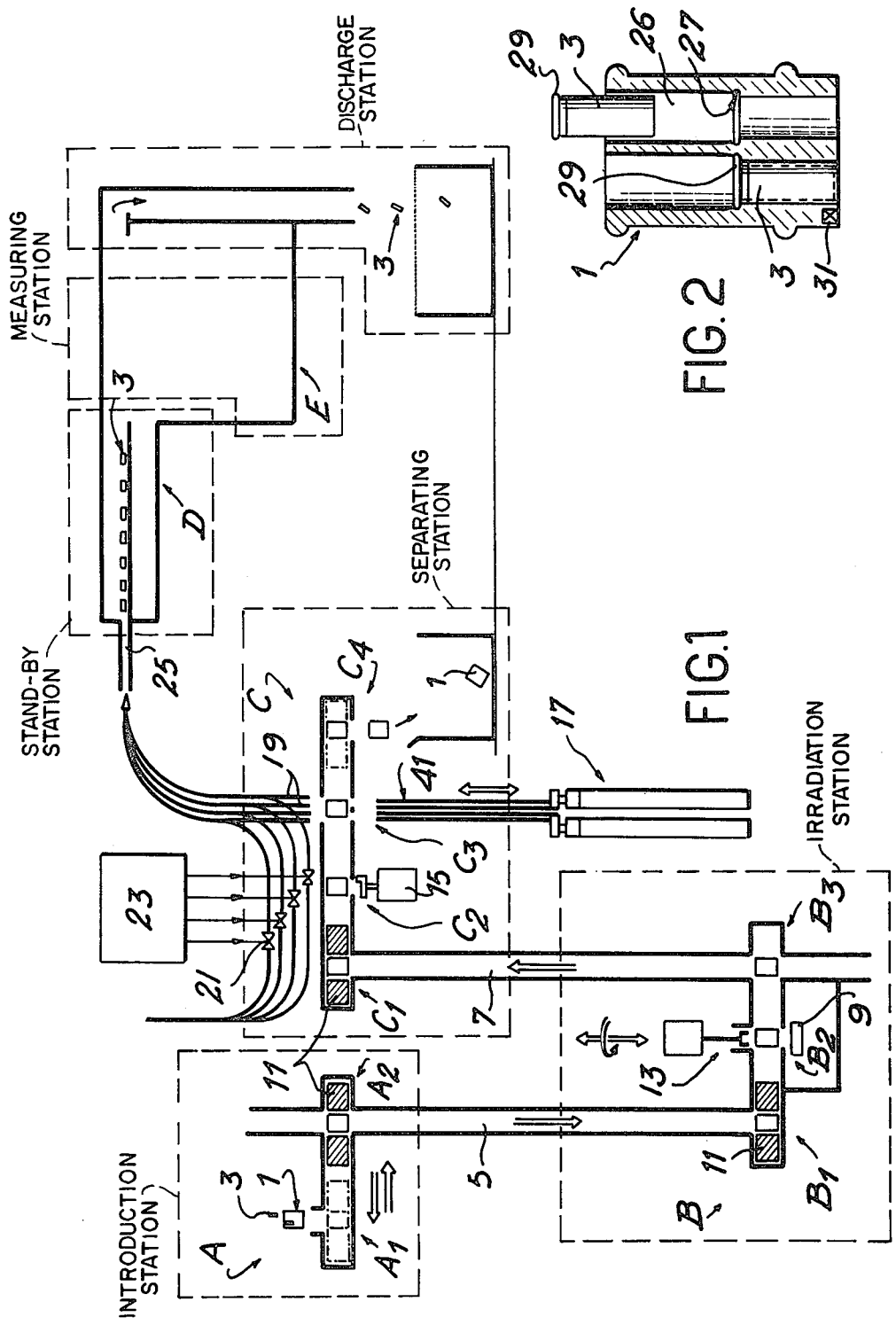

METHOD AND DEVICE FOR ACTIVATION ANALYSIS

This invention relates to a method of activation analysis and to an analytical device for the application of the method.

It is known that the analysis of a sample by activation consists in inducing an activity in the sample by irradiation, then in detecting and measuring the characteristic radiations emitted by the radioactive isotopes produced by the activation. This makes it possible to establish both the qualitative and quantitative composition of the sample by means of the number, the nature and the energy of the radiations emitted by the radioactive isotopes.

By reason of the growth and decay of activity of the radioactive isotopes formed, it is appropriate to note the importance of the time parameter in a method of this type. In fact, the performances of this method depend at the same time on the activity induced within the sample (which is a function in particular of the irradiation time), on the number of integrated signals (which is a function of the measuring time) and on the time which elapses between irradiation and commencement of the measurement in order to allow "cooling" of the sample (and in order to permit disappearance of the short-lived isotopes which would be liable to interfere with the measurement).

As is also known, it is a customary practice to analyze a large number of samples one after the other (routine analysis). Activation and measurement of the activity of each sample are performed for equal periods of time; this makes it possible to obtain an optimum rate of analysis since it is possible to subject one of the samples to irradiation while carrying out at the same time the measurement of a sample which has previously been irradiated.

In this type of analysis, high rates can therefore be attained only by adopting short irradiation and measurement times, with the result that a satisfactory degree of accuracy cannot always be obtained at the same time. In fact, an increase in the rate of analysis by reduction of the measuring or irradiation time results in weakening of the signal since both the induced activity and the number of integrated signals are reduced.

Moreover, it is not always possible for reasons of a technical or economic order to employ an irradiation flux of higher intensity or a detector of higher efficiency for the purpose of obtaining a higher rate of analysis while maintaining a good standard of accuracy.

The precise aim of the present invention is to provide a method of activation analysis which makes it possible to attain considerably higher rates than those which could be obtained by the known method of the prior art in respect of an equal degree of accuracy or alternatively to achieve excellent performances which were not permitted by the method of the prior art in respect of an equal rate of analysis, this result being achieved without entailing the need for more stringent conditions of irradiation or detection.

This method of activation analysis which consists in known manner in measuring the radiations emitted by samples after they have been irradiated is characterized in that N samples are irradiated simultaneously and that said samples are each measured in turn after having been separated from each other, the irradiation time $t$ being N times longer than the time of measurement of a sample.

Simply by modifying the time measurement of the method having the above-mentioned characteristics as a function of the number N of samples irradiated simultaneously and of the time interval $t/N$ adopted for each measurement, it is possible to carry out analyses at any desired rate and in some cases at a high rate while maintaining a sufficient degree of accuracy which is compatible with the results sought. In order to obtain the desired rate of analysis and/or the desired sensitivity of measurement, the experimenter who employs the method according to the invention therefore has two parameters which he can select according to requirements, namely the irradiation time $t$ and the number N of samples irradiated simultaneously.

By irradiating N samples simultaneously for a period of time $t$ and by measuring the radiations emitted by each sample during a time interval $t/N$, it is possible for example to increase the rate of analysis by reducing the time interval $t/N$, knowing that the accuracy of measurements is a function of the choice of the values attributed respectively to $t$ and N. It is also possible in accordance with the invention to increase the performances of analysis by increasing the number N of samples in respect of a given rate of analysis. In this case, the ratio $t/N$ which characterizes the measuring time is maintained constant and the irradiation time $t$ and the number of irradiated samples N are increased simultaneously. Since the irradiation time $t$ has been increased in respect of the same reading time $t/N$, it can readily be ascertained that a higher degree of accuracy of measurements is thus achieved.

By way of explanatory illustration, there will now be described one example of application of the method in accordance with the invention, whereby the rate adopted in an activation analysis according to the method of the prior art as recalled in the foregoing can be multiplied by a factor $n$ by making a judicious choice of the number N of samples while maintaining a signal which is substantially identical with the signal obtained in the prior art at a low rate of analysis.

In order to multiply by a factor $n$ the rate of analysis of the prior art corresponding to times of irradiation and measurement of a sample which are equal to $\theta$, the measurement of one of the N samples which are irradiated simultaneously should be carried out during a time interval $\theta/n$ at the time of application of the method according to the invention. In order to maintain an analytical signal at a substantially constant value at the time of increase in the rate of analysis, the operation must be performed with a number N of samples which is equal to $n^2$.

In fact, if $\theta$ and $t$ are respectively the irradiation times in the prior art and in the invention, and if $\theta$ and $t/N$ are the corresponding measurement times, the multiplication of the rate of analysis by $n$ entails the need to ensure that $$\theta/n = t/N \tag{1}$$

Should it be desired to maintain the same sensitivity, it is necessary to compensate for the division by $n$ of the measurement time by a multiplication of the irradiation time by the same factor $n$, which is written $$n\theta = t \tag{2}$$

The comparison between the equalities (1) and (2) necessarily leads to the condition $N = n^2$.

The comparative results which are grouped together in Table 1 and obtained at the time of analyses performed with a measurement time of 2 minutes and with a meaurement time of 1 minute (double rate) in the case of a half-life of the isotopes concerned of 10 minutes, clearly show that the signals recorded in the case of a double rate by applying the method according to the invention are very close in value to the signal recorded at a low rate, which is very far from the result achieved by the method employed in the prior art. In other words, by applying the method of the invention and in order to double the rate of analysis ($n = 2$) while maintaining substantially the same performances, it is only necessary to choose $N = n^2 = 4$ samples.

It should be noted that, at the time of analysis of each of the four samples, the activity decay times which are variable from one sample to another have naturally been taken into account.

TABLE I

Comparison of performances

| | Conventional $\int$ method | | Method of the invention |
|---|---|---|---|
| Duration of a measurement | 2 mins (single rate) | 1 min. (double rate) | 1 min. (double rate) |
| Time of irradiation | 1 sample/ 2 mins. | 1 sample/ 1 min. | 4 samples/ 4 mins. |
| Activity of each sample at the end of irradiation | A | 0.52 A | 1.87 A |
| Signal measured on each sample | X | 0.27 X | 1st sample 0.97 X<br>2nd sample 0.91 X<br>3rd sample 0.84 X<br>4th sample 0.79 X |

This invention also relates to a device for carrying out the method in accordance with the invention.

The analytical device for carrying out this method comprises in known manner a transfer circuit, for example of the pneumatic type, in which there is provided in succession an introduction station, an irradiation station, an optional stand-by station, a measuring station and a discharge station, said device being primarily distinguished by the fact that the portion of said circuit which is located upstream of the stand-by station (or upstream of the measuring station if no provision is made for a stand-by station) is adapted to the transfer of a sample-holder which is capable of receiving N samples and that said device further comprises downstream of the irradiation station, a separating station provided with means for positioning the sample-holder and with means for extracting said samples from said sample-holder.

A device of this type has the advantage of simple design since it results from the judicious adaptation of a transfer circuit of known type to activation analysis in order to permit simultaneous transfer of a plurality of samples in front of the irradiation target in accordance with the method of the invention while ensuring position-location of said samples before they pass successively in front of the detector, thus making it possible to take into account the different isotope decay times in the case of each sample.

In order to gain a clearer understanding of the invention, the following description relates to one example of practical application of the device and of the method in accordance with the invention, this example being given without implying any limitation whatsoever, reference being made to the accompanying drawings, in which:

FIG. 1 is a general diagram of the analytical device in accordance with the invention;

FIG. 2 is a detail view of the sample-holder;

Figure 3:
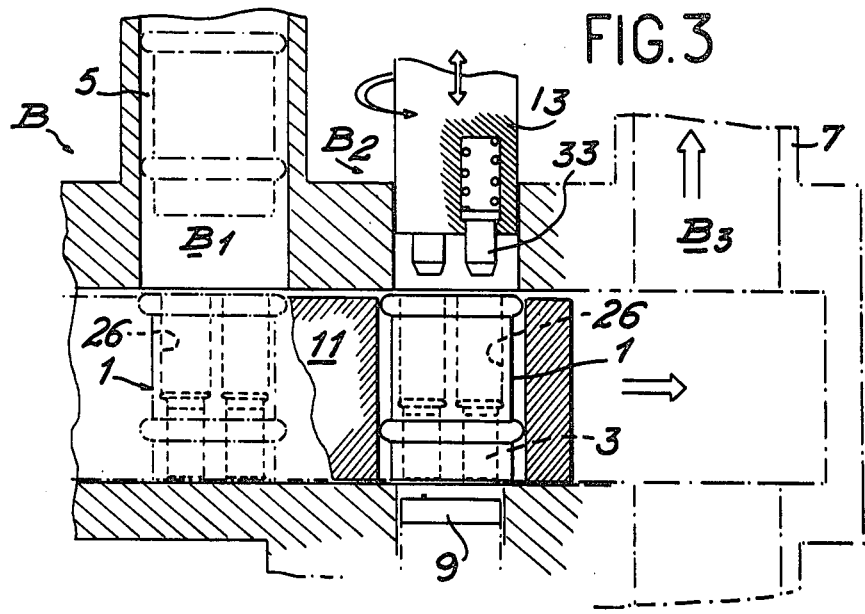
FIG. 3 is a view of the irradiation station.

There is shown in FIG. 1 the entire transfer circuit provided with stations which are suited to the application of each stage of the method of analysis according to the invention, said stations being connected to each other by means of pneumatic tubes.

In accordance with the essential feature of the invention, the introduction station A, the irradiation station B and the separating station C are adapted to a sample-holder 1 for maintaining capsules 3 which contain the samples. The pneumatic transfer tubes 5 and 7 which interconnect the different stations A, B and C are also adapted to the circulation of said sample-holder 1.

It is seen that the introduction station has two positions: the introduction position $A_1$ proper of the sample-holder 1 and the starting position $A_2$ from which said sample-holder 1 is transferred to the irradiation station B by the pneumatic tube 5.

The irradiation station B has three positions: the position $B_1$ for receiving the sample-holder 1 as this latter leaves the tube 5, the exposure position $B_2$ located in front of the radiation source 9, the starting position $B_3$ from which the sample-holder 1 is transferred to the separating station C by the tube 7.

The separating station C has four positions: the position $C_1$ for receiving the sample-holder 1 as this latter leaves the tube 7, the position $C_2$ for the orientation of the sample-holder, the position $C_3$ for extracting capsules from the sample-holder and the position $C_4$ for discharging the sample-holder after removal of the capsules 3.

Within the different stations, drawers 11 permit transfer of the sample-holder from one position to the next.

Before giving a detailed description of the composition of the stations A, B and C and the constructional design of the sample-holder 1, it can be noted that FIG. 1 shows the location of the rotating tube 13 which can be introduced into the position $B_2$ of the irradiation station B when the sample-holder 1 is present at this location. Similarly, the figure shows the location of the positioning device 15 beneath the position $C_2$ of the separating station C and the location of the extracting jack 17 beneath the position $C_3$ of said station C.

Pneumatic tubes such as the tube 19 which are equal in number to the capsules 3 placed within the sample-holder 1 extend from the position $C_3$ of the separating-station C.

The tubes 19 into which the capsules 3 are discharged are each fitted with a valve 21 actuated by means of the control device 23.

Said tubes 19 open into a pneumatic tube 25 which leads to the stand-by station D, this station being followed by the measuring station E.

At the time of operation, a device of this type in fact makes it possible to subject a plurality of samples to simultaneous irradiation at $B_2$, to locate said samples at $C_2$ by suitably positioning the sample-holder, to extract the samples from the sample-holder at $C_3$ and then to perform successive measurements on each sample in the final station E in a predetermined order. In fact, the samples which are injected into the tube 25 in succession by virtue of the action of the valves 21 controlled by means of the positioning operation carried out at $C_2$ and as a function of the program of analysis pass through the stations D and E in a well-determined order.

The sample-holder 1 as a whole is shown in FIG. 2. Said sample-holder has a certain number of cylindrical recesses 26 for capsules 3 having the same shape and containing the samples to be analyzed. Said recesses 26 which are machined in the sample-holder 1 are distributed on a circle, the center of which is located on the axis of said sample-holder 1. Said recesses are provided with lateral grooves 27 corresponding to the retaining rims 29 of the capsules 3. In addition, a magnetic pastille 31 is incorporated in the mass of the sample-holder 1 at the base of this latter.

FIG. 3 shows the irradiation station B and more precisely the positions $B_1$ and $B_2$ of said station.

Provision is made in the bottom portion of the position $B_2$ for the irradiation source 9 and in the top portion of said position for a rotating tube 13 fitted with telescopic pins 33 which can be introduced into the recesses 26 of the sample-holder 1 above the capsules 3. Said rotating tube 13 is connected to a motor (not shown) for driving said tube in rotation.

After transfer to position $B_2$ of the sample-holder 1 containing the capsules 3 which are rigidly maintained in position by insertion of the retaining rims 29 of the capsules within the grooves 27, the samples contained in the capsules 3 are irradiated in a uniform manner by causing the sample-holder 1 to be driven in rotation by means of the rotating tube 13.

Figure 4:
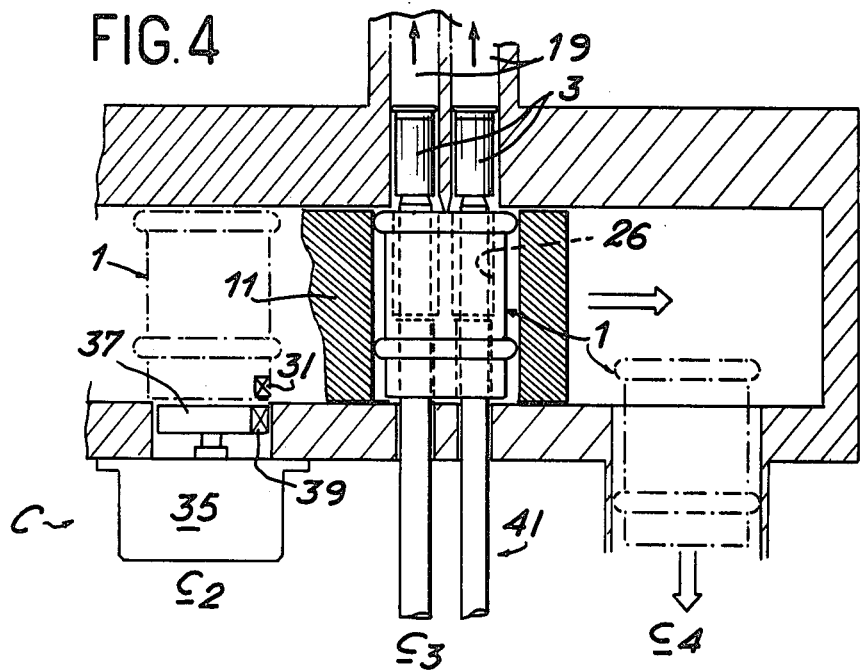
FIG. 4 is a view of the separating station.

FIG. 4 shows the sample-separating station C. The position $C_2$ of said station is located above the sample-holder positioning device 15 comprising the motor 35, there being mounted above said motor the rotary plate 37 which is fitted with a magnet 39. The position $C_3$ of the station C is placed above the extraction jack 17 which is provided with vertically moving rods 41, said rods being equal in number to the recesses 26 which are machined in the sample-holder 1.

At $C_2$, the sample-holder is thus oriented so as to locate the samples since, in point of fact, when the motor 35 carries out a revolution (or a number of revolutions), said sample-holder is displaced and then stopped in the position in which the magnetic plate 31 is located opposite to the magnet 39 of the plate 37.

At $C_3$, the samples are extracted from the sample-holder 1 and introduced into the tubes 19 as a result of the thrust exerted by the rods 41 of the extraction jack 17 as these latter are displaced in the upward direction.

The samples are then injected as a function of their position on the sample-holder and successively into the single tube 25 through which they are conveyed into the stand-by station D and measuring station E. These stations D and E are provided with known means for displacing the samples through these latter in succession.

In order to make use of the method according to the invention for the practical application of the example which has been given by way of illustration in the description of the method, it is possible to employ four capsules having a diameter of 10 mm and a height of 20 mm, which is equivalent to a volume of approximately 1.5 cm³. Dimensions of this order permit satisfactory irradiation of four samples by means of the target of a neutron generator whose active diameter is 30 mm, a target of this type being commonly employed in activation processes.

It is apparent that the pneumatic systems for transferring sample-holders and separate samples have been described by way of explanation and that the invention is not limited to their use in any respect whatsoever.

Similarly, the scope of the invention extends to embodiments in which the distribution of stationary and movable elements is different from the arrangement described, especially in which the irradiation source is capable of moving with respect to stationary samples.

We claim:

1. A method of activation analysis of N samples, wherein the N samples are irradiated simultaneously and wherein said N samples are each measured in turn after having been separated from each other, the irradiation time being N times longer than the time of measurement of one sample.

2. A method of activation analysis according to claim 1, wherein the rate of analysis is modified by changing at least one of the two parameters: time $t$ of irradiation of samples and number N of samples.

3. A method of activation analysis according to claim 2, wherein the rate of analysis is increased by reducing the time $t/N$ of measurement of a sample.

4. A method of activation analysis according to claim 1, wherein the performances of the analysis are enhanced by increasing the number N of samples in respect of a given rate of analysis determined by a given time of measurement $t/N$.

5. A device for activation analysis, wherein said device is constituted by a transfer circuit comprising means for the simultaneous irradiation of N samples carried on a sample-holder, means for locating each of the N samples on the sample-holder, means for extracting each of the N samples from the sample-holder, means for measuring sequentially each of the N samples in a predetermined order, means to position the sample-holder adjacent the irradiation, the locating and the measuring means, and means to move each of the samples extracted from the sample-holder to a position adjacent the measuring means.

6. An analytical device according to claim 5, wherein said transfer circuit is pneumatic.

7. An analytical device according to claim 5, wherein the sample-holder comprises a certain number of recesses for capsules disposed at intervals on a circumference whose center is located on the axis of said sample-holder.

8. An analytical device according to claim 5, wherein the irradiation means comprises means for displacing the sample-holder in rotational motion when said sample-holder is located in said irradiation station.

9. An analytical device according to claim 5, wherein the extracting means comprises a jack provided with movable arms equal in number to recesses on the sample-holders.

10. A device for activation analysis, wherein said device is constituted by a transfer circuit comprising successively an introduction station, an irradiation station, a separating station, an optional stand-by station, a measuring station and a discharge station, that portion of said transfer circuit which is located upstream of said stand-by station being adapted to the transfer of a sample-holder which is capable of receiving N samples and said separating station being provided with means for positioning the sample-holder and with means for extracting said samples from said sample-holder said means for positioning the sample-holder constituting a magnetic element rigidly fixed to the sample-holder and a magnet which produces action on said magnetic element the magnet being located on a rotary plate driven by a motor.

* * * * *